United States Patent
King et al.

(10) Patent No.: US 7,921,488 B2
(45) Date of Patent: Apr. 12, 2011

(54) MATTRESS HAVING VERTICAL AIR CELLS WITH THERMOREGULATION

(75) Inventors: Rachel H. King, Harrison, OH (US); Mayur Yermaneni, Shrewsbury, MA (US); Gregory W. Branson, Batesville, IN (US); Todd P. O'Neal, Fairfield, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 199 days.

(21) Appl. No.: 11/909,178

(22) PCT Filed: Mar. 24, 2006

(86) PCT No.: PCT/US2006/010857
§ 371 (c)(1),
(2), (4) Date: Oct. 7, 2009

(87) PCT Pub. No.: WO2007/008260
PCT Pub. Date: Jan. 18, 2007

(65) Prior Publication Data
US 2010/0017961 A1    Jan. 28, 2010

Related U.S. Application Data

(60) Provisional application No. 60/665,241, filed on Mar. 25, 2005, provisional application No. 60/665,141, filed on Mar. 25, 2005.

(51) Int. Cl.
*A47C 21/04* (2006.01)
*A61F 7/00* (2006.01)

(52) U.S. Cl. .................. 5/421; 5/423; 5/706; 5/710

(58) Field of Classification Search ............. 5/421, 423, 5/706, 710
See application file for complete search history.

(56) References Cited

U.S. PATENT DOCUMENTS

| | | |
|---|---|---|
| 1,121,277 A | 12/1914 | Theresa |
| 2,932,491 A | 4/1960 | Miller |
| 3,295,594 A | 1/1967 | Hopper |
| 3,714,947 A | 2/1973 | Hardy |
| 4,114,620 A | 9/1978 | Moore et al. |
| 4,523,594 A | 6/1985 | Kuznetz |
| 4,864,671 A * | 9/1989 | Evans ............... 5/710 |
| 6,565,699 B1 | 5/2003 | Szczesuil |
| 6,606,754 B1 | 8/2003 | Flick |
| 6,730,115 B1 | 5/2004 | Heaton |
| 6,855,158 B2 * | 2/2005 | Stolpmann ............. 5/421 |
| 6,945,987 B2 | 9/2005 | Beard et al. |
| 2003/0079488 A1 | 5/2003 | Bieberich |

FOREIGN PATENT DOCUMENTS
WO    WO02/29348    4/2002

* cited by examiner

*Primary Examiner* — Robert G Santos
*Assistant Examiner* — Brittany M Wilson
(74) *Attorney, Agent, or Firm* — Barnes & Thornburg LLP

(57) ABSTRACT

A thermoregulating apparatus (20) for exchanging thermal energy with and supporting a patient (24) and method of exchanging thermal energy is provided. The apparatus includes a heat exchange fluid circuit (30, 95, 102) located below a patient support layer (44) for exchanging thermal energy with the patient.

25 Claims, 5 Drawing Sheets

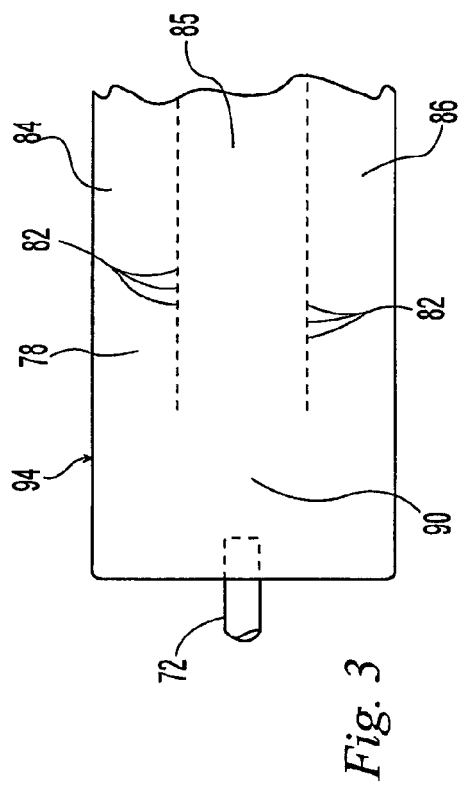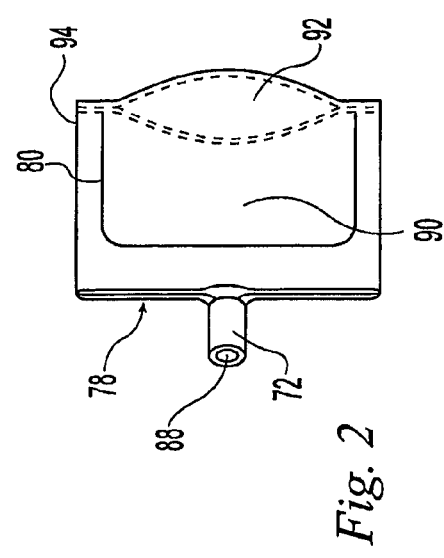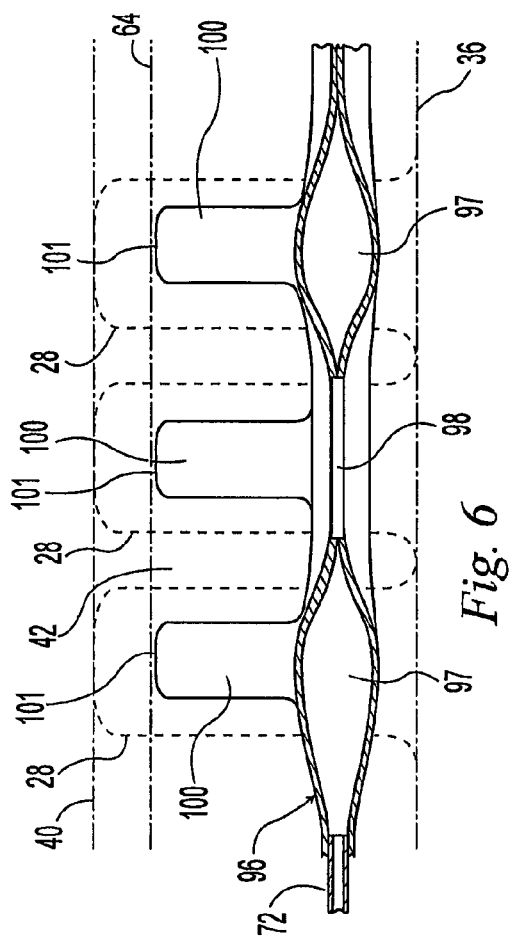

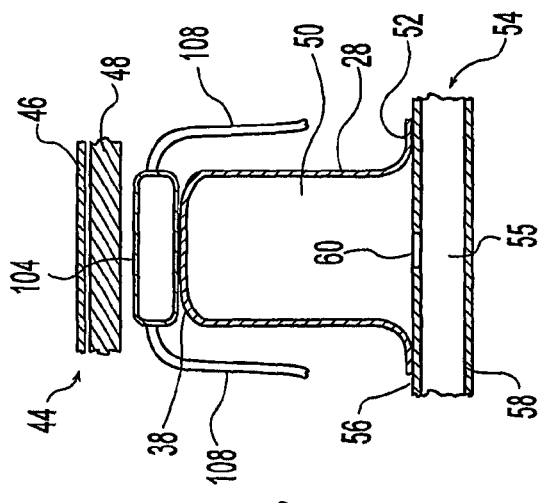
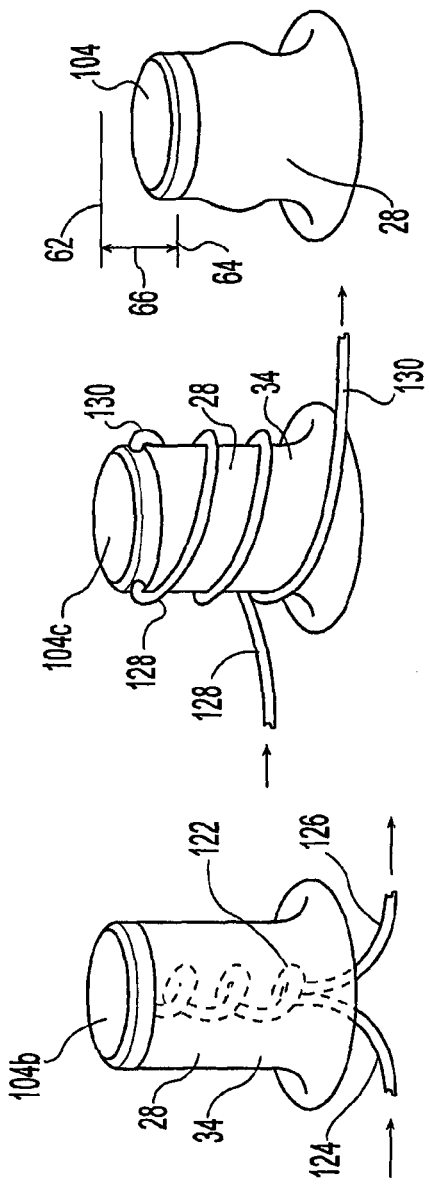

MATTRESS HAVING VERTICAL AIR CELLS WITH THERMOREGULATION

CROSS REFERENCE TO RELATED APPLICATIONS

This application is the U.S. national phase of PCT/US2006/010857 filed Mar. 24, 2006. PCT/US2006/010857 claims priority to U.S. Ser. No. 60/665,241, filed Mar. 25, 2005 and to U.S. Ser. No. 60/665,141, filed Mar. 25, 2005. The entireties of U.S. Ser. No. 60/665,241 and U.S. Ser. No. 60/665,141 are hereby incorporated herein by reference. This application is also related to U.S. Ser. No. 11/909,240, which is the U.S. national phase of PCT/US2006/010805 filed Mar. 24, 2006, which also claims priority to U.S. Ser. No. 60/665,241 and U.S. Ser. No. 60/665,141.

BACKGROUND

The present invention relates to thermoregulating devices and, more particularly, to thermoregulating devices that may be used to cool or warm a patient.

It is sometimes desirable in the treatment of a patient to either cool or warm the patient. For example, it may be clinically desirable to cool patients who have suffered a stroke or cardiac arrest. In other circumstances, such as when a patient is suffering from hypothermia, it can be desirable to warm the patient.

SUMMARY OF THE INVENTION

One embodiment takes the form of a thermoregulating apparatus for exchanging thermal energy with and supporting a patient. The apparatus includes a plurality of gas-filled support cells, a flexible patient support layer and a heat exchange fluid circuit. The support cells each have a lower portion and an upward facing surface. The lower portions of the support cells together define a lower boundary of the plurality of support cells. The upward facing surfaces of the support cells are resiliently compressible towards the lower portions. The patient support layer spans the plurality of support cells and is located above and proximate the upward facing surfaces of the plurality of support cells. Each of the support cells is resiliently compressible in response to the weight of a patient being supported on the patient support layer. The heat exchange fluid circuit is disposed between the patient support layer and the lower boundary of the support cells proximate the plurality of support cells and exchanges thermal energy with the patient through the patient support layer.

In some embodiments, the heat exchange fluid circuit includes a plurality of bladders. Each of the bladders are disposed between a respective one of the upward facing surfaces of the plurality of support cells and the patient support layer. The plurality of bladders are independently and vertically displaceable as the plurality of support cells are resiliently compressed in response to the patient supported on the patient support layer.

In some embodiments, the heat exchange fluid circuit is disposed below the upward facing surfaces of the plurality of support cells. In still other embodiments, each of the upward facing surfaces of the support cells are resiliently compressible from a fully extended position to a compressed position. The fully extended position and the compressed position of each the support cell is vertically spaced above the lower boundary. The fully extended position is located above the compressed position. The range between the fully extended position and the compressed position defines a normal operating range of the plurality of support cells. The heat exchange fluid circuit is disposed below the compressed positions.

In some embodiments, each of the support cells are substantially cylindrical with a substantially vertically extending axis.

In some embodiments, the thermoregulating apparatus is a low air loss apparatus.

In some embodiments, the support cells are filled with air and substantially impermeable to air.

In some embodiments, the heat exchange fluid circuit includes at least one inlet port and at least one outlet port. The heat exchange fluid circuit is operably couplable to an external heat exchange unit through the at least one inlet port and the at least one outlet port.

Another embodiment takes the form of a thermoregulating apparatus for exchanging thermal energy with and supporting a patient which includes a plurality of gas-filled support cells and a heat exchange fluid circuit. The support cells each have a lower portion and an upward facing surface wherein the lower portions together define a lower boundary of the support cells and the upward facing surfaces are resiliently compressible towards the lower portions. The heat exchange fluid circuit includes a plurality of bladders wherein each of the bladders is associated with one of the support cells. Each of the bladders is independently displaceable together with its associated support cell.

In some embodiments, the fluid circuit comprises a plurality of flexible fluid conduits fluidly coupling the plurality of bladders. The fluid conduits each define a conduit cross sectional flow area and the bladders each define a bladder cross sectional flow area. The bladder cross sectional flow areas are greater than the conduit cross sectional flow areas.

In some embodiments, the plurality of flexible conduits each include a substantially helical portion fluidly coupled to a respective one of the bladders.

In some embodiments, the helical portion is disposed within a respective one of the support cells.

In some embodiments, each of the plurality of flexible conduits fluidly couples a pair of the bladders. The flexible conduits each have a length sufficient to allow independent vertical movement of the pair of bladders.

In some embodiments, the thermoregulating apparatus further comprises a flexible patient support layer spanning the plurality of support cells. The patient support layer supported on the plurality of support cells and each of the support cells is resiliently compressible in response to the patient supported on the support layer.

In some embodiments, the plurality of support cells have a substantially cylindrical shape and a vertical axis.

Yet another embodiment takes the form of a thermoregulating apparatus for exchanging thermal energy with and supporting a patient wherein the apparatus has a plurality of gas-filled support cells and a heat exchange fluid circuit. Each of the gas-filled support cells has a lower portion and an upward facing surface. The upward facing surfaces of the support cells are resiliently compressible towards the lower portions. The lower portions of the support cells together define a lower boundary of the plurality of support cells and the upward facing surfaces of the support cells together define an upper boundary of the plurality of support cells. The support cells define an interstitial space located laterally between the support cells and vertically between the upper and lower boundaries. At least a portion of the heat exchange fluid circuit is located within the interstitial space and is spaced downwardly from the upper boundary.

The support cells are compressible from a fully extended position to a compressed position wherein the range between the fully extended position and the compressed position define a normal operating range of the support cells. In some other embodiments, the heat exchange fluid circuit may be located in the interstitial space and at a position that is below compressed position of the support cells.

In some embodiments, each of the support cells are substantially cylindrical and have a vertical axis.

In some embodiments, the apparatus is a low air loss apparatus.

In some embodiments, the support cells are filled with air and are substantially impermeable to air.

In some embodiments, the fluid circuit defines a generally serpentine path through the interstitial space.

Another embodiment takes the form of a method of exchanging thermal energy with an object which includes providing an apparatus having a plurality of support cells and a heat exchange fluid circuit including a plurality of bladders. The object is supported on the apparatus with the plurality of support cells being individually compressed to facilitate the equalization of a support pressure generated by the weight of the object. The method also includes associating each of the plurality of bladders with one of the plurality of support cells, independently adjusting the position of each of the bladders in response to the compression of the support cells, circulating a heat exchange medium through the fluid circuit, and exchanging thermal energy between the object and the heat exchange medium.

In some embodiments, the support cells are substantially cylindrical and define a substantially vertical axis. Each of the plurality of bladders are positioned on an upper surface of a respective one of the support cells.

Yet another embodiment takes the form of a method of exchanging thermal energy with an object which includes providing an apparatus having a plurality of support cells that together define an upper boundary and a lower boundary. The object is supported on the apparatus with the plurality of support cells being individually compressed to facilitate the equalization of a support pressure generated by the weight of the object. The method also includes positioning a heat exchange fluid circuit in the apparatus between the upper boundary and the lower boundary at a location spaced sufficiently below the upper boundary that compression of the plurality of support cells by the object does not impinge upon the fluid circuit, circulating a heat exchange medium through the fluid circuit, and exchanging thermal energy between the object and the heat exchange medium In some embodiments of the method, the support cells are substantially cylindrical and define a substantially vertical axis.

In some embodiments of the method, the fluid circuit defines a generally serpentine path within an interstitial space defined between the plurality of support cells.

The object in each of these methods may be a human, e.g., a medical patient.

BRIEF DESCRIPTION OF THE DRAWINGS

The detailed description particularly refers to the accompanying Figs. in which:

FIG. 2 is a partial perspective view of an inlet line and bladder that forms the heat exchange fluid circuit in the apparatus of FIG. 1.

FIG. 3 is a side view of the inlet line and bladder of FIG. 2.

FIG. 5 is a top view of fluid circuit for a heat exchange medium that can be mounted in a patient support apparatus having a plurality of gas-filled support cells.

FIG. 6 is a cross sectional view of a portion of the fluid circuit shown in FIG. 5.

FIG. 8 is a cross sectional view of a portion of a thermoregulating apparatus incorporating the support cells and bladders of FIG. 7.

FIG. 9 is a perspective view of another embodiment of a support cell having a heat exchange fluid circuit bladder mounted thereon.

FIG. 10 is a perspective view of yet another embodiment of a support cell having a heat exchange fluid circuit bladder mounted thereon.

FIG. 11 is a perspective view of still another embodiment of a support cell having a heat exchange fluid circuit bladder mounted thereon.

FIG. 12 is a perspective view of a support cell in a compressed position resulting from a load applied thereto.

Figure 1:
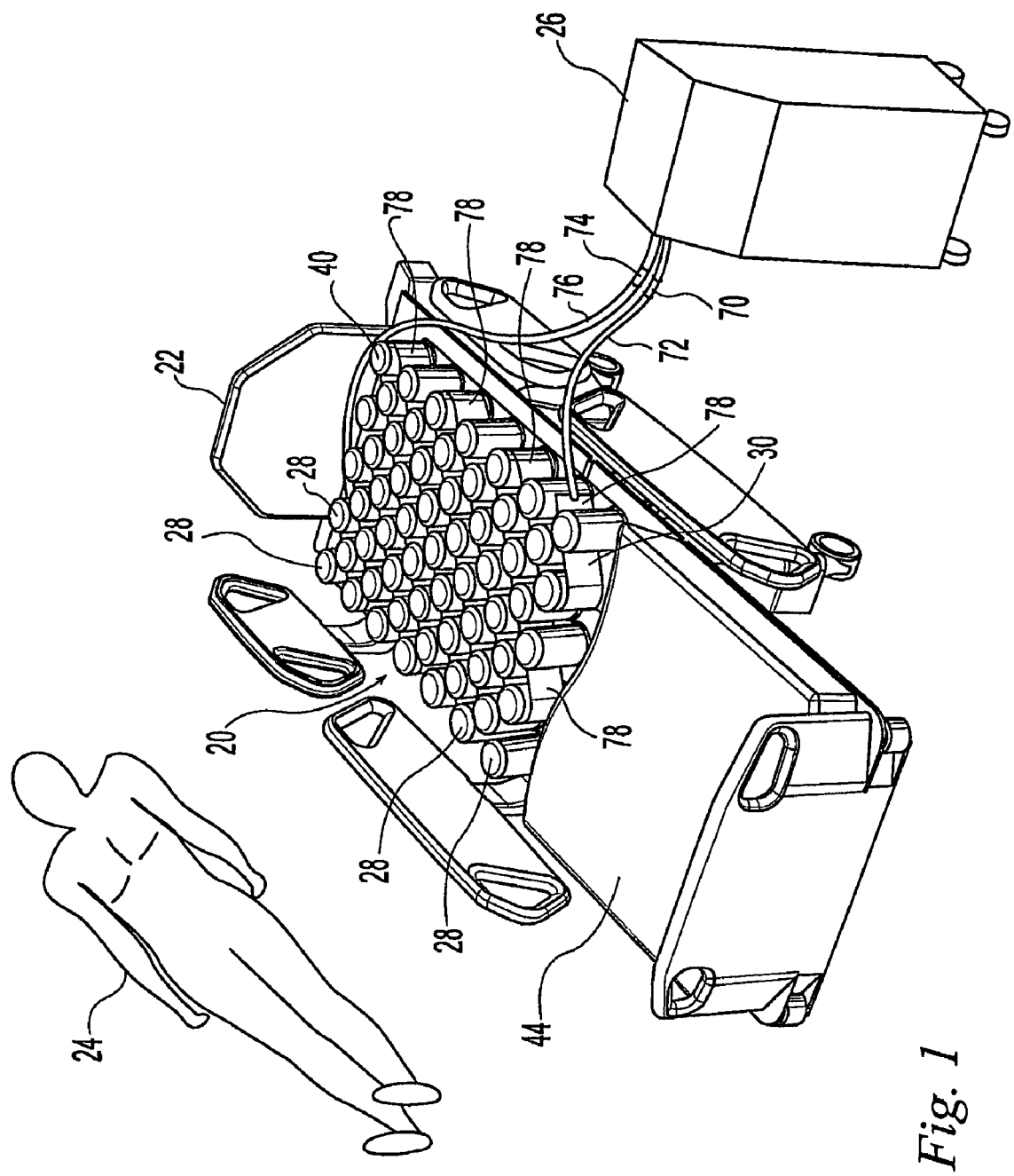
FIG. 1 is a partially cut away and exploded perspective view of a hospital bed with a thermoregulating apparatus and a patient.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION OF THE INVENTION

A thermoregulating apparatus 20 for use with a hospital bed 22 and patient 24 is shown in FIG. 1. In the treatment of patient 24 it may be desirable to either chill or warm patient 24 and apparatus 20 can be employed for this purpose. A conventional heat exchange unit 26 is coupled with apparatus 20 to circulate a heat exchange medium, e.g., water, through apparatus 20. Heat exchange units 26 are well known in the art and may include a compressor, a condenser and evaporator. Water, or other heat exchange medium employed with apparatus 20, may be chilled by exchanging thermal energy with the evaporator or the water may be warmed by exchanging thermal energy with the condenser. A pump located in unit 26 then circulates the water through apparatus 20.

When a patient is supported on a mattress or similar support surface it is desirable to equalize the support pressure at key pressure points on the patient (e.g., the back of the head and heals of the patient). If the support pressure is not spread over a larger area of the patient at these key pressure points, the resulting pressure concentrations increase the likelihood that the patient will experience pressure ulcers or similar undesirable effects. It is known to provide patients with a patient support structure containing gas- or fluid-filled chambers that facilitate the equalization of the pressure supporting the patient. Such patient support structures can be broadly categorized as powered, non-powered, or low-air loss systems. Non-powered air surfaces contain air-filled chambers that do not provide for the intentional loss of air from within the chambers and do not require a continuous source of air to be supplied to the chambers. The PrimeAire® ARS Pressure Relief Mattress commercially available from Hill-Rom Company, Inc. having a place of business in Batesville, Ind. is an example of such a non-powered air surface. Low-air loss systems are a form of powered surfaces that employ air-filled chambers that are designed to allow a small quantity of air to continuously escape from the chambers during use. An air supply unit is used with such low-air loss systems to maintain the air-filled chambers at a desired pressure. The Acucair® Continuous Airflow System commercially available from Hill-Rom Company, Inc. having a place of business in Batesville, Ind. is an example of such a low-air loss system. In all of these types of patient support structures, the air- or fluid-filled chambers facilitate the equalization of the pressure used to support the patient and it is common to use such patient support structures to minimize the risk of pressure ulcers.

Conventional thermoregulating devices for chilling or warming a patient do not provide the pressure-equalization features of a patient support having air- or fluid-filled chambers. Consequently, the benefits of such patient support structures are generally not obtainable if a conventional thermoregulating device is placed between the patient and the patient support structure.

In the illustrated embodiment, apparatus 20, as best seen in FIG. 1, combines a plurality of gas-filled support cells 28 with a heat exchange fluid circuit 30 to provide a thermoregulating device which supports patient 24 in a manner that facilitates the equalization of support pressure, in other words, it facilitates the reduction of the peak pressure the patient experiences at key pressure support locations.

Figure 4:
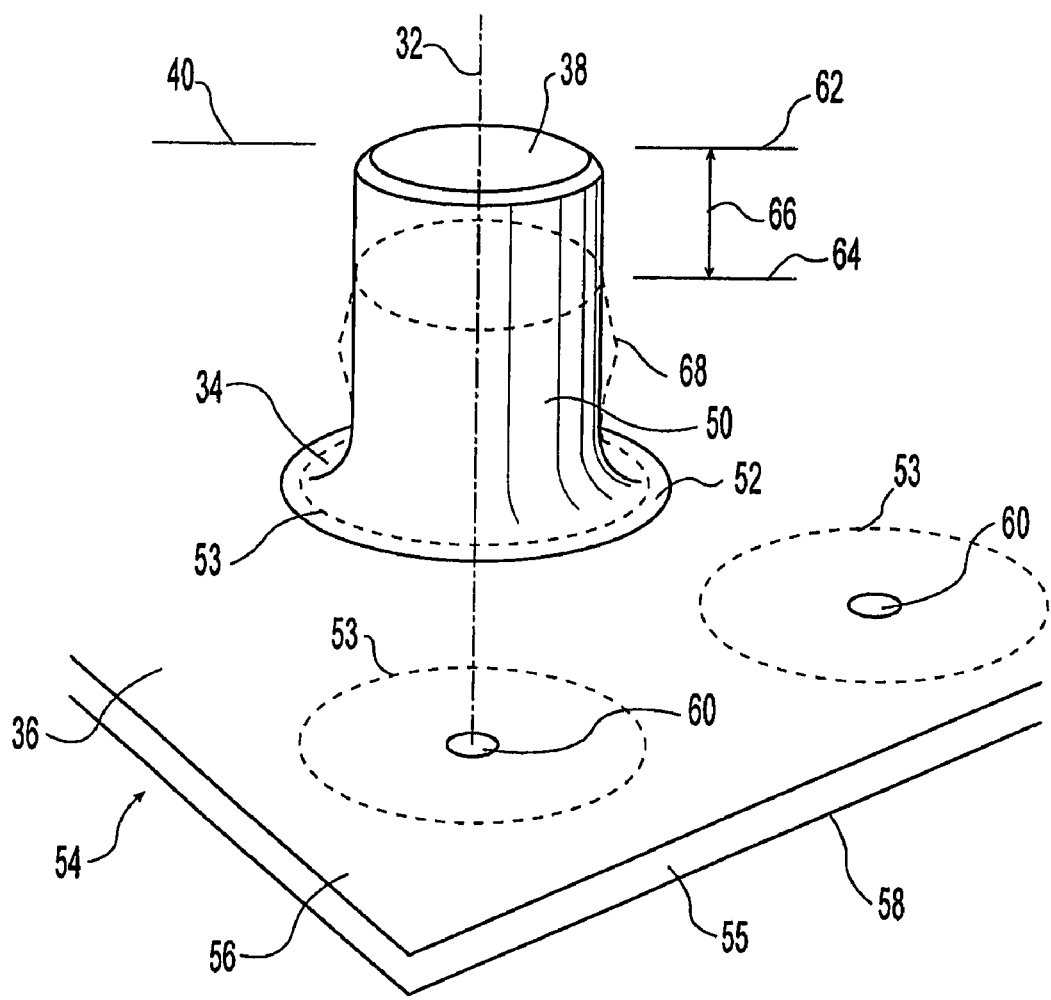
FIG. 4 is an exploded perspective view of a support cell.

As shown in FIG. 4, the illustrated gas-filled support cells 28 have a substantially cylindrical shape with a vertically oriented axis 32. Although the illustrated cells 28 have a substantially cylindrical shape, other shaped-cells maybe used, such as rectangular or octagonally shaped cells.

Each of the cells 28 has a lower portion 34 that together define a lower boundary 36 of the support cells 28. The cells 28 also each have an upward facing surface 38 that together define an upper boundary 40. Upper and lower boundaries 40, 36 define the vertical limits of interstitial space 42 located laterally between support cells 28. Upward facing surfaces 38 lie in a generally horizontal plane in the illustrated embodiments. Upward facing surfaces 38, however, are not required to be positioned horizontally and other configurations of upward facing surfaces 38 which are oriented to face generally upwardly to receive a weight load, e.g., from patient support layer 44, can also be employed with the present invention.

An individual support cell 28 is shown in greater detail in FIG. 4. Support cells 28 are formed out of a polymeric material such as polyurethane and have a hollow interior volume 50 which is filled with a gas. In the illustrated embodiment, cells 28 are filled with air. Cells 28 include a radial flange 52 that is welded to upper sheet 56 of plenum layer 54 using radio frequency welding to form an air tight bond. Dashed lines 53 indicate the location of the weld. Plenum layer 54 is shown in exploded view in FIG. 4 and includes an upper sheet 56 and lower sheet 58 that are joined together, e.g., by radio frequency welding, along their outer perimeter to form an air chamber or plenum 55. Openings 60 in upper sheet 56 provides fluid communication between plenum 55 and the interior volumes 50 of each of the support cells 28. Upper sheet 56 also defines the lower boundary 36 of support cells 28. In the illustrated embodiment, sheets 56, 58 are polyurethane film sheets.

Apparatus 20 may take the form of a powered, a non-powered, or a low air loss mattress. In all forms, support cells 28 are generally non-permeable to air. In non-powered air surface embodiments, plenum layer 54 is also non-permeable to air and, by providing fluid communication between the inner volumes 50 of each of the support cells 28, maintains each of the support cells 28 at a substantially equivalent pressure under differing load conditions. In other words, when a large load is placed on apparatus 20, the internal pressure within volume 50 of each of the support cells 28 will be increased including those cells 28 which do not have a load placed directly on their upper surfaces 38.

In low air loss mattress embodiments, an upper plenum sheet 56 is used that permits the limited passage of air therethrough. A separate air supply is coupled to plenum 55 to provide a continuous supply of air thereto to replenish the air lost through sheet 56 and maintain plenum 55, and thus interior volumes 50, at a desired pressure. The flow of air through patient support layer 44 generated by the loss of air through upper sheet 56 beneficially removes moisture from those portions of layer 44 in direct contact with patient 24 as is well-known to those having ordinary skill in the art.

Weight loads placed on apparatus 20 are transferred through patient support layer 44 to the upward facing surfaces 38 of the support cells 28. In powered, non-powered, and low air loss embodiments, each individual support cell 28 is compressed to an extent that is determined by the load placed on it. Upward facing surfaces 38 are resiliently compressed towards lower portion 34. In other words, when the load compressing surfaces 38 is removed, surfaces 38 will return to their fully extended positions.

FIG. 4 provides a schematic illustration of the response of an individual support cell to a load being placed on surface 38. Line 64 indicates the position of surface 38 when support cell 28 has been compressed by a maximum design load placed on surface 38 and takes the shape indicated by dashed lines 68. Line 62 indicates the position of surface 38 when support cell 28 is in its fully extended position without an external load being placed thereon. For smaller loads, support cell 28 will be compressed to a lesser extent and surface 38 will be positioned somewhere between compressed position 64 and fully extended position 62 within normal operating range 66. The pressure within volume 50 and dimensions of support cell 28, together with the value chosen for the maximum design load, will determine the magnitude of range 66. The maximum design load will be chosen based upon the anticipated patient support loads. The anticipated load will differ depending upon whether apparatus 20 intended for use with bariatric patients, children or adults.

Apparatus 20 also includes a patient support layer 44 overlaying support cells 28 and on which patient 24 is supported. In FIG. 1, that portion of support layer 44 which overlays the fluid circuit 30 has been cutaway to better illustrate fluid circuit 30. A cross sectional view of support layer 44 is shown in FIG. 8 and includes an upper layer of ticking 46 and a lower layer 48 of support material. Ticking 46 is a conventional mattress ticking material. Lower layer 48 includes a three dimensional material or fiber network and/or a conventional open cell urethane foam. Suitable three dimensional material is commercially available from Freudenberg & Co. headquartered in Weinheim an der Bergstrasse, Germany. Lower layer 48 is designed to promote the transfer of thermal energy between patient 24 and fluid circuit 30 or for other reasons. In other embodiments, lower layer 48 may be omitted.

Patient support layer 44 is sufficiently loose and flexible so that when a patient 24 is supported on layer 44, layer 44 will generally conform to the body of patient 24 as it transfers the weight of patient 24 to support cells 28. Support cells 28 are gas-filled and the interior volume 50 of cells 28 are interconnected so that the pressure of the gas in each of the cells 28 of the mattress or in a particular zone of a mattress remains substantially equal. Thus, as the weight of patient 24 is supported by individual support cells 28, those cells 28 which have a particularly high load initially placed thereon will have their upward facing surface 38 compressed toward lower portion 34 and the patient begins to bear more forcefully on adjacent cells 28 until the load on the peak loaded cell has diminished and the gas pressure within each of the cells 28 is balanced with the load placed on their upward facing surfaces 38. Thus, those individual cells 28 that are located at the key pressure points of patient 24 will be compressed to a greater extent than the adjacent support cells 28 to thereby spread some of the weight load experienced by the most significantly compressed support cell 28 to adjacent support cells 28. By this differential compression of the individual support cells 28, support cells 28 spread the weight load placed on apparatus 20 by patient 24 over a larger area and facilitate the reduction of the peak support pressures experienced by the patient 24.

Heat exchange fluid circuit 30 defines a serpentine path through interstitial space 42 about support cells 28 and is shown in greater detail in FIGS. 2 and 3. In apparatus 20 illustrated in FIG. 1, fluid circuit 30 is located only in that portion of apparatus 20 which would support the upper torso of a typical patient 24. In alternative embodiments, however, fluid circuit 30 could extend either throughout the entirety of apparatus 20 or through only a more limited area of apparatus 20. Flexible, elongate fluid conduits provide an inlet line 72 and outlet line 74 coupled to a bladder 78 to define circuit 30. In the illustrated embodiment, elongate conduits 72, 74 are plastic tubes, e.g., polyvinylchloride (PVC) or polyurethane tubes, having a nominal inner diameter of 0.25 inches (0.64 cm). Conventional coupling members define an inlet port 70 and outlet port 74 of fluid circuit 30 and connect fluid circuit to heat exchange unit 26.

In the illustrated embodiment, water is the heat exchange medium that is circulated through circuit 30. Water entering port 70 flows through inlet line 72 to bladder 78. After flowing through bladder 78, the water enters outlet tube 76 and passes through outlet port 74 as it is returned to heat exchange unit 26. In unit 26, the water is either chilled or warmed depending upon whether it is desired to chill or warm patient 24. As the water passes through bladder 78 it exchanges thermal energy with patient 24 through support layer 44. For example, if unit 26 is used to chill the water, the water will absorb thermal energy from patient 24 thereby cooling patient 24 and warming the water as the water passes through bladder 78. In some situations it may be desirable to place a second thermoregulating device on top of the patient 24 when chilling or warming a patient with apparatus 20.

As best seen in FIGS. 2 and 3, illustrated bladder 78 is formed by joining two sheets of polyurethane film together along their outer perimeter to form a water tight seal with radio frequency weld 80. Intermittent welds 82 are used to join the opposite sides of bladder 78 together at a more central location and to maintain bladder 78 in a generally vertical configuration when placed between support cells 28. Intermittent welds 82 define three flow channels 84, 85, 86 within bladder 78. The intermittent spacing of welds 82, however, allows a limited quantity of fluid to pass vertically between channels 84, 85, 86. An inlet area 90 without intermittent welds is located between inlet tube 72 and flow channels 84, 85, 86. As seen in FIG. 2, inlet tube 72 has a cross sectional flow area 88 that is less than the cross sectional flow area 92 defined by bladder 78. Thus, as water enters bladder 78 from inlet tube 72, the velocity of the water will be reduced. The reduction of velocity of the water facilitates the exchange of thermal energy between the water within bladder 78 and the surrounding environment including patient 24. The discharge end of bladder 78 coupled to outlet line 76 has a configuration which is the same as the inlet end shown in FIG. 2.

Bladder 78 is positioned within interstitial space 42 with its uppermost edge 94 positioned below compressed position 64 of surface 38 which defines the lower limit of normal operating range 66. By positioning uppermost edge 94 below normal operating range 66, bladder 78 will not be impinged upon by layer 44 and will not interfere with the support of patient 24 during normal usage of apparatus 20.

Another embodiment of a heat exchange fluid circuit which may be positioned in the interstitial space 42 between support cells 28 and below normal operating range 66 is shown in FIGS. 5 and 6. Fluid circuit 95 includes a bladder 96 which receives chilled or warmed water through inlet line 72 and discharges the water through outlet line 76. Bladder 96 is formed by joining two polymeric film sheets, e.g., polyurethane film sheets, together to define an interior volume 97 through which the water, or other heat exchange medium, flows. Bladder 96 has a plurality of openings 98 through which support cells 28 extend. Bladder 96 also includes upright column members 100 which each have a hollow interior in communication with the remainder of bladder interior 97. Column members 100 are attached to the upper sheet of bladder 96 and are located between support cells 28 to increase the volume of water within interstitial space 42 and thereby promote the exchange of thermal energy between the water and patient 24. The interior volume of column members 100 are in fluid communication with remainder of bladder interior 97 to permit water to enter and be discharged from columns 100. The uppermost surface 101 of columns 100 are located below compressed position 64 so that columns 100 do not interfere with the support of patient 24 on layer 44. In alternative embodiments of fluid circuit 95, interior baffle members or other suitable means may be positioned within interior volume 97 to direct and control the flow of water within bladder 96.

Figure 7:
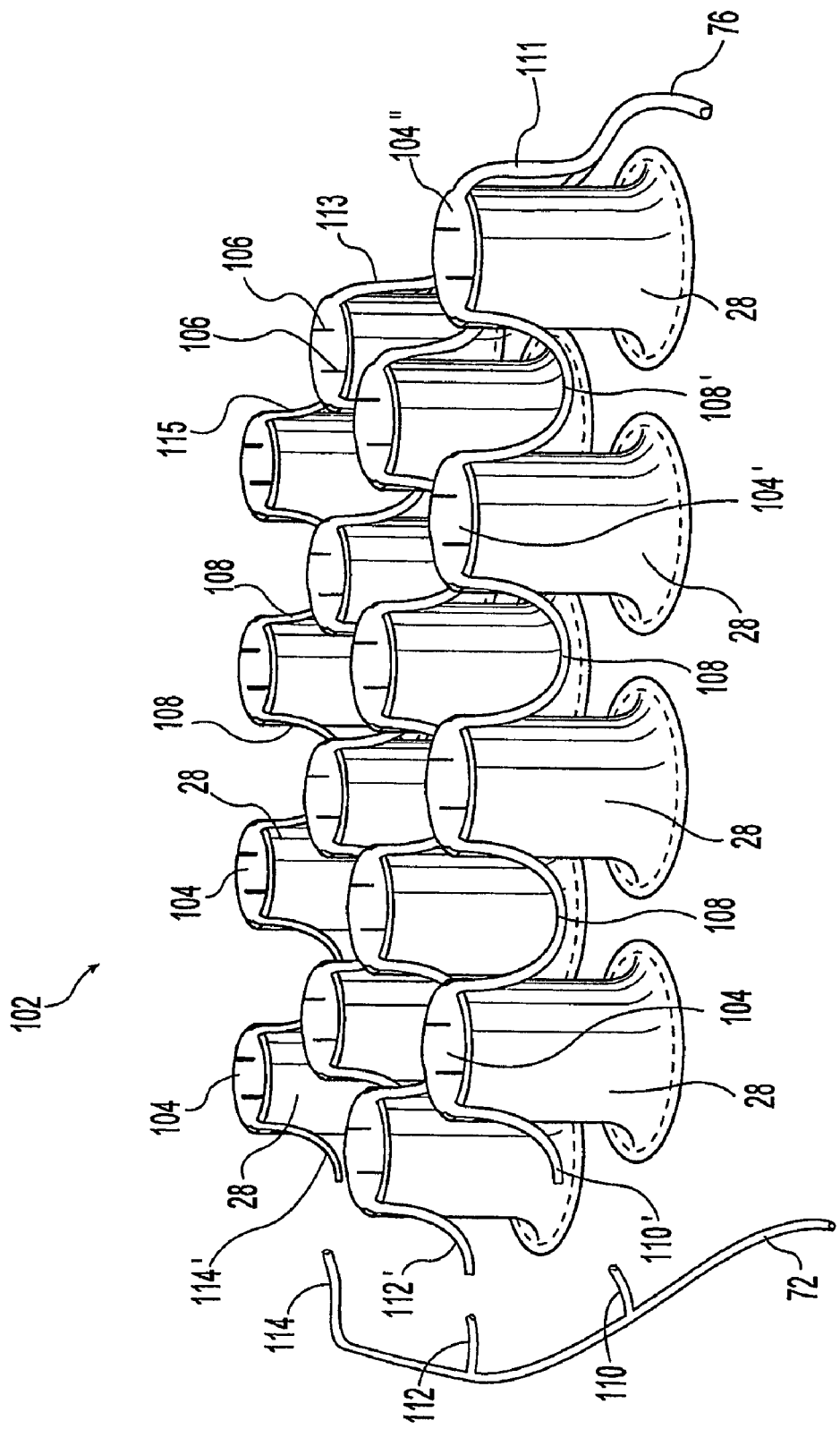
FIG. 7 is a perspective view showing a plurality of support cells having heat exchange fluid circuit bladders mounted thereon.

Another embodiment of the fluid circuit is shown in FIG. 7. The fluid circuit 102 depicted in FIG. 7 includes a plurality of bladders 104 each of which are mounted one of the support cells 28 and disposed between upward facing surface 38 and patient support layer 44. As best with reference to FIG. 12, bladders 104 are vertically displaceable as the support cell 28 on which they are mounted are compressed and move through normal operating range 66. The support cells 28 depicted in FIG. 7 are all in their fully extended positions. The fluid pressure within bladders 104 is greater than the gas pressure within support cell 28. Thus, when bladder 104 transfers a load from support layer 44 to support cell 28, it is support cell 28 that is deformed and compressed downwardly. When such a load is applied to support cell 28 through bladder 104, the interior volume of bladder 104 is not collapsed but remains open allowing fluid to continue to flow through bladder 104 due to the higher pressure in bladder 104. The pressure exerted by bladder 104 on layer 44 in an upward direction, however, is limited by the upward force exerted by the lower pressure gas within volume 50 of support cell 28 which acts on bladder 104.

The individual bladders 104 are fluidly coupled with flexible elongate conduits which can be arranged in one long series, or, as shown in FIG. 7, small sets of bladders 104 can be arranged in parallel. In FIG. 7, inlet line 72 functions as a header with three tubes 110, 112 and 114 branching therefrom in a parallel arrangement. Each tube 110, 112, 114 conveys water to a linear series of bladders 104 which are interconnected by fluid lines 108. (In the break away view of FIG. 7, tube 110 is fluidly coupled to tube 110' through intermediately located bladders 104 and tubes 108. Similarly, tube 112 is fluidly coupled to tube 112' and tube 114 is fluidly coupled to tube 114'.) Outlet line 74 receives the fluid discharged from lines 111, 113 and 115 and conveys it to heat exchanger 26 where it is either chilled or warmed and returned to inlet line 72.

Fluid lines 108 are flexible tubes which, as can be seen in FIG. 7, have a length that is sufficient to allow a pair of adjacent bladders 104 connected by a fluid line 108, e.g., bladders 104', 104" connected by fluid line 108', to allow for the independent vertical movement or displacement of the bladders 104', 104". As can also be seen in FIG. 7, the flow of fluid through bladders 104 is directed in a substantially Z-shaped flow path by radio frequency welds 106 which join the opposite walls of bladders 104. The cross sectional area of the flow path defined by bladders 104, however, remains larger than that of fluid lines 108. Radio frequency welds, adhesives or other suitable means may be used to secure bladders 104 to support cells 28.

Three alternative embodiments of bladders 104a, 104b, 104c and connecting fluid lines are shown in FIGS. 9-11 which also allow for the independent vertical displacement of the bladders as the support cells 28 on which the individual bladders are mounted are individually compressed and move through normal operating range 66. In the embodiment illustrated in FIG. 9, the inlet line 118 and outlet line 120 coupled to bladder 104a extend through the interior volume 50 of support cell 28. The inlet line 118 and outlet line 120 are joined together to form a double line 116 within volume 50. Each of the lines forming double line 116 is fluidly coupled to bladder 104a through its bottom surface and has a length that is sufficient to allow support cell 28 to reach its fully extended position. Instead of utilizing a double line 116 having two fluid lines joined side-by-side, a double lumen line, with a first smaller diameter fluid line located within an outer fluid line could alternatively be provided to couple inlet 118 and outlet 120 with bladder 104a. Lines 116, 118 extend through openings 60 (not shown in FIG. 9) to connect bladder 104a with an adjacent bladder or other fluid line of the heat exchange fluid circuit.

In the embodiment of FIG. 10, the fluid lines in communication with bladder 104b are arranged in a generally helical shape and are also located within interior volume 50 of support cell 28 on which the bladder is mounted. Inlet line 124 and outlet line 126 extend through opening 60 into the interior volume 50 of support cell 28. Helical line portion 122 fluidly couples inlet line 124 and outlet line 126 to bladder 104b without restricting the movement of support cell 28 through its normal operating range 66. Helical line portion 122 may either have two lines joined side-by-side as depicted, or, in alternative configurations, be a double lumen line.

In the embodiment of FIG. 11, the inlet line 128 and outlet line 130 in fluid communication with bladder 104c are wound about the outer surface of support cell 28 in a substantially helical pattern and are located in interstitial space 42.

FIG. 12 shows an exemplary support cell 28 in a compressed position 64 as described above with regard to FIG. 4. Bladder 104 remains substantially above cell 28 during compression of cell 28. Lines 62 and 64 generally represent the upper and lower bounds, respectively, of the normal operating range 66 of support cell 28.

The present invention has been described with reference to certain exemplary embodiments, variations, and applications. However, it is understood that the present invention is defined by the appended claims. It may be modified within the spirit and scope of this disclosure. This disclosure is therefore intended to cover any and all variations, uses, or adaptations of the present invention using its general principles.

What is claimed is:

1. A thermoregulating apparatus for exchanging thermal energy with and supporting a patient, the apparatus comprising:
   a plurality of gas-filled support cells, each of the support cells having a lower portion and an upward facing surface, the upward facing surfaces of the support cells being resiliently compressible towards the lower portions, the lower portions of the plurality of support cells together defining a lower boundary of the plurality of support cells;
   a flexible patient support layer spanning the plurality of support cells, the patient support layer disposed above and proximate the upward facing surfaces of the plurality of support cells, the patient being supportable on the patient support layer wherein each of the support cells is resiliently compressible in response to the patient being supported on the patient support layer; and
   a heat exchange fluid circuit disposed between the patient support layer and the lower boundary proximate the plurality of support cells; the fluid circuit exchanging thermal energy with the patient through the patient support layer; wherein the heat exchange fluid circuit includes a plurality of bladders, each of the bladders being disposed between a respective one of the upward facing surfaces of the plurality of support cells and the patient support layer, the plurality of bladders being independently vertically displaceable as the plurality of support cells are resiliently compressed in response to the patient being supported on the patient support layer.

2. The apparatus of claim 1 wherein at least a portion of a plurality of tubes of the heat exchange fluid circuit is disposed below the upward facing surfaces of the plurality of support cells.

3. The apparatus of claim 1 wherein each of the upward facing surfaces of the support cells are resiliently compressible from a fully extended position to a compressed position, the fully extended position and the compressed position of each the support cell being vertically spaced above the lower boundary, the fully extended position being located above the compressed position, the range between the fully extended position and the compressed position defining a normal operating range of the plurality of support cells; and
   wherein at least a portion of the heat exchange fluid circuit is disposed below the compressed positions.

4. The apparatus of claim 1 wherein each of the support cells are substantially cylindrical with a substantially vertically extending axis.

5. The apparatus of claim 1 wherein the apparatus is a low air loss apparatus.

6. The apparatus of claim 5 wherein the support cells are filled with air and are substantially impermeable to air.

7. The apparatus of claim 1 wherein the heat exchange fluid circuit includes at least one inlet port and at least one outlet port, the heat exchange fluid circuit being operably couplable to an external heat exchange unit through the at least one inlet port and the at least one outlet port.

8. A thermoregulating apparatus for exchanging thermal energy with and supporting a patient, the apparatus comprising:
   a plurality of gas-filled support cells, the support cells each having a lower portion and an upward facing surface, the upward facing surfaces of the support cells being resiliently compressible towards the lower portions, the lower portions of the plurality of support cells together defining a lower boundary of the plurality of support cells; and a heat exchange fluid circuit, the fluid circuit including a plurality of bladders, each of the bladders being associated with a respective one of the plurality of support cells, each of the bladders being independently displaceable together with the associated support cell;

wherein the fluid circuit comprises a plurality of flexible fluid conduits fluidly coupling the plurality of bladders, the fluid conduits each defining a conduit cross sectional flow area and the bladders each defining a bladder cross sectional flow area, the bladder cross sectional flow areas being greater than the conduit cross sectional flow areas; wherein each of the plurality of flexible conduits fluidly couples a pair of the bladders, the flexible conduits each having a length sufficient to allow independent vertical movement of the pair of bladders.

9. The apparatus of claim 8 further comprising a flexible patient support layer spanning the plurality of support cells, the patient support layer being supported on the plurality of support cells and wherein each of the support cells is resiliently compressible in response to the patient being supported on the support layer.

10. The apparatus of claim 8 wherein the plurality of support cells have a substantially cylindrical shape and a vertical axis.

11. A thermoregulating apparatus for exchanging thermal energy with and supporting a patient, the apparatus comprising:

a plurality of gas-filled support cells, the support cells each having a lower portion and an upward facing surface, the upward facing surfaces of the support cells being resiliently compressible towards the lower portions, the lower portions of the plurality of support cells together defining a lower boundary of the plurality of support cells; and a heat exchange fluid circuit, the fluid circuit including a plurality of bladders, each of the bladders being associated with a respective one of the plurality of support cells, each of the bladders being independently displaceable together with the associated support cell; wherein the fluid circuit comprises a plurality of flexible fluid conduits fluidly coupling the plurality of bladders, the fluid conduits each defining a conduit cross sectional flow area and the bladders each defining a bladder cross sectional flow area, the bladder cross sectional flow areas being greater than the conduit cross sectional flow areas; wherein the plurality of flexible conduits each include a substantially helical portion fluidly coupled to a respective one of the bladders.

12. The apparatus of claim 11 wherein the helical portion is disposed within a respective one of the support cells.

13. A thermoregulating apparatus for exchanging thermal energy with and supporting a patient, the apparatus comprising:

a plurality of gas-filled support cells extending upwardly from an underlying layer, each of the support cells having a lower portion, an upward facing surface, the upward facing surfaces of the support cells being resiliently compressible towards the lower portions, the lower portions of the plurality of support cells together defining a lower boundary of the plurality of support cells and the upward facing surfaces of the support cells together defining an upper boundary of the plurality of support cells, the plurality of support cells defining an interstitial space located laterally between the plurality of support cells and vertically between the upper and lower boundaries; and a heat exchange fluid circuit, at least a portion of the fluid circuit disposed within the interstitial space, the fluid circuit being spaced downwardly from the upper boundary, wherein the heat exchange fluid circuit comprises an elongated ribbon-like structure that is routed through the interstitial space next to each of the plurality of support cells with opposite side surfaces of the ribbon-like structure being oriented generally vertically and a bottom edge of the ribbon-like structure being supported by the underlying layer.

14. The apparatus of claim 13 wherein each of the upward facing surfaces of the support cells are resiliently compressible from a fully extended position to a compressed position, the fully extended position and the compressed position of each the support cell being vertically spaced above the lower boundary, the fully extended position being located above the compressed position, the range between the fully extended position and the compressed position defining a normal operating range of the plurality of support cells; and wherein the heat exchange fluid circuit is disposed below the compressed positions.

15. The apparatus of claim 13 wherein each of the support cells are substantially cylindrical and have a vertical axis.

16. The apparatus of claim 13 wherein the apparatus is a low air loss apparatus.

17. The apparatus of claim 16 wherein the support cells are filled with air and are substantially impermeable to air.

18. The apparatus of claim 13 wherein the fluid circuit defines a generally serpentine path through the interstitial space.

19. A method of exchanging thermal energy with an object, the method comprising:

providing an apparatus having a plurality of support cells and a heat exchange fluid circuit including a plurality of bladders, wherein each of the plurality of bladders are positioned on an upper surface of a respective one of the support cells;

supporting the object on the apparatus wherein the plurality of support cells are individually compressible to facilitate the equalization of a support pressure generated by support of the object;

associating each of the plurality of bladders with a respective one of the plurality of support cells and independently adjusting the position of each of the plurality of bladders in response to the compression of the support cells;

circulating a heat exchange medium through the fluid circuit; and exchanging thermal energy between the object and the heat exchange medium.

20. The method of claim 19 wherein the object is a human.

21. The method of claim 19 wherein the support cells are substantially cylindrical and define a substantially vertical axis and wherein each of the plurality of bladders are positioned on an upper surface of a respective one of the support cells.

22. A method of exchanging thermal energy with an object, the method comprising:

providing an apparatus having a plurality of support cells extending upwardly from an underlying layer, the plurality of support cells together defining an upper boundary and a lower boundary, the apparatus also having a heat exchange fluid circuit between the upper boundary and the lower boundary and spaced sufficiently below the upper boundary that compression of the plurality of support cells by the object does not impinge upon the fluid circuit, wherein the heat exchange fluid circuit comprises an elongated ribbon-like structure that is routed through an interstitial space defined next to each of the plurality of support cells with opposite side surfaces of the ribbon-like structure being oriented generally vertically and a bottom edge of the ribbon-like structure being supported by the underlying layer;

supporting the object on the apparatus wherein the plurality of support cells are individually compressible to facilitate the equalization of a support pressure generated by support of the object;

circulating a heat exchange medium through the fluid circuit; and exchanging thermal energy between the object and the heat exchange medium.

23. The method of claim 22 wherein the object is a human.

24. The method of claim 22 wherein the support cells are substantially cylindrical and define a substantially vertical axis.

25. The method of claim 22 wherein the fluid circuit defines a generally serpentine path within an interstitial space defined between the plurality of support cells.

\* \* \* \* \*